United States Patent
Bakeev et al.

(10) Patent No.: US 6,242,518 B1
(45) Date of Patent: *Jun. 5, 2001

(54) METHOD FOR PREVENTING OR RETARDING THE FORMULATION OF GAS HYDRATES

(75) Inventors: Kirill N. Bakeev, Ringwood; Randall Myers, Lincoln Park; Jui-Chang Chuang, Wayne; Thomas Winkler, Maywood; Allen Krauss, Clifton, all of NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/553,929

(22) Filed: Apr. 21, 2000

(51) Int. Cl.$^7$ .................................. C07C 7/00; C07C 7/20
(52) U.S. Cl. ............................... 524/376; 137/3; 137/13; 585/950

(58) Field of Search ............................. 524/376; 585/950; 137/3, 13

(56) References Cited

U.S. PATENT DOCUMENTS 6,117,929 * 9/2000 Bakeev et al. .................... 524/376

* cited by examiner

*Primary Examiner*—P. Hampton-Hightower
(74) *Attorney, Agent, or Firm*—Walter Katz; William J. Davis; Marilyn J. Maue

(57) ABSTRACT

A composition for preventing or retarding the formation of gas hydrates during the transport of a fluid comprising water and a hydrocarbon through a conduit. The composition is a homopolymer of vinyl caprolactam, or copolymers thereof, having a low molecular weight in the range of 500 to 4000, which is made by polymerization of the monomer or monomers in a polymerization solvent which is a mixture of a glycol ether and water, preferably 2-butoxyethanol and water, at a pH of about 8–12.

10 Claims, No Drawings

METHOD FOR PREVENTING OR RETARDING THE FORMULATION OF GAS HYDRATES

CROSS-REFERENCE TO RELATED U.S. PATENT APPLICATIONS

This application is related to co-pending U.S. patent application, Ser. No. 09/204,768, filed Dec. 3, 1998, which describes the preparation of an inhibitor composition by polymerizing vinyl caprolactam in 2-butoxyethanol solvent.

BACKGROUND OF THE INVENTION

1. Field of the Invention

The invention relates to a method for preventing or retarding the formation of gas hydrates, or for reducing the tendency of such hydrates to agglomerate, during the transport of a fluid comprising water and a hydrocarbon through a conduit, and, more particularly, to the addition to the fluid of a composition of a low molecular weight vinyl caprolactam polymer, or copolymers thereof, which is made in a defined polymerization solvent, to inhibit such gas hydrate formation.

2. Description of the Prior Art

It is well known in the art that the formation of gas hydrates in a conduit, e.g. in a pipeline, where an aqueous phase is inherently present, during the transport of liquids such as oil, and of gases, particularly lower hydrocarbons, e.g. methane, ethane, propane, butane, isobutane and natural gas, is a serious problem, especially in areas with a low temperature in the winter season or in the sea. Generally, the ambient temperatures in such areas are so low that gas hydrates are formed in the gas transportation pipeline, due to the inevitable presence of co-produced water therein. Insulation of the pipelines may decrease the opportunity for gas hydrate formation; however, if the field is relatively small and some distance from the production facilities, the cost of providing suitable insulation is too high to make such a field economically attractive. It is also known to add anti-freeze compounds, for example, ethylene glycol or methanol, during transport of such liquids and gases to minimize gas hydrate formation; however, large quantities of these highly flammable compounds are required to be effective which is expensive and unsafe.

Further representative of the prior art in this field are U.S. Pat. Nos. 4,915,176; 5,420,370; 5,432,292; and 5,723,524; EPO 0323774A1; EPA 0457375A1; EPA 0526929A1; Can. Pat. Appln. 2,073,577; "Gas Hydrates and Hydrate Prevention", 73 GPA Annual Convention, pages 85–93; WO 96/08456; WO 96/08636; WO 93125798; WO 94/12761; WO 95/17579; and WO 95/32356.

Representative of such art is the disclosure in U.S. Pat. No. 5,723,524 that poly(vinyl caprolactam) (PVCL), synthesized in isopropanol, and having an average molecular weight of 36,000 amu, as determined by gel permeation chromatography (GPC), using polyethylene glycol as standard, is a gas hydrate inhibitor.

Accordingly, it is an object of this invention to provide an improved composition and method for retarding the formation of gas hydrate in a hydrocarbon gas pipeline.

SUMMARY OF THE INVENTION

What is described herein is a composition for effectively preventing or retarding the formation of gas hydrates, or for reducing the tendency of gas hydrates to agglomerate, during the transport of a fluid comprising water and a hydrocarbon, through a conduit. The composition comprises a vinyl caprolactam homopolymer (PVCL), or copolymers thereof, for example, copolymers with vinyl pyrrolidone (VP), having a low molecular weight of about 500 to about 4000, which are made by polymerizing the monomer or monomers in a polymerization solvent which is a mixture of a glycol ether containing an alkoxy group having at least 3 carbon atoms, and preferably, 2-butoxyethanol (BGE), and water, preferably in a predetermined weight ratio, at a pH of about 8–12.

DETAILED DESCRIPTION OF THE INVENTION

The polymer which exhibits advantageous inhibitory characteristics in the composition of the invention is a homopolymer of vinyl caprolactam, or copolymer thereof, having a molecular weight of about 500 to about 4000, as determined by GPC using polyethylene glycol as the standard.

The composition of the invention may also include low molecular weight copolymers of vinyl caprolactam with one or more monomers selected from N-vinylpyrrolidone; acrylamide; N-alkyl acrylamides, e.g. N,N-dimethyl acrylamide; N-[1-(2-pyrrolidonylethyl)] acrylamide; N,N-dialkyl aminoalkyl methacrylamide, e.g. N,N-dimethylamino propyl methacrylamide; N,N-dialkyl aminoalkyl (meth)acrylates; e.g. N,N-dimethylaminoethyl (meth)acrylate and quaternized salts thereof, including N-alkyl halides and the like; 4-vinylpyridine; N-methyl-N-vinylacetamide; N-vinylacetamide; and N-vinylformamide. The homopolymer of vinylcaprolactam is preferred.

Generally, the polymer solution used in the composition of the invention is present in an amount of about 30 to 60%, preferably 45 to 55%, by weight in admixture with the solvent. The polymer inhibition concentration in the pipeline, i.e. in the aqueous phase, water being inherently present therein, is about 0.1 to 3%, preferably 0.5–1%, by weight. The solvent* inhibition concentration, accordingly, is about 1 to 9% by weight of the aqueous phase.

* total of all solvents present in the composition

The polymer is synthesized from its monomer, or monomers, in a polymerization solvent which is a predetermined mixture of a glycol ether containing an alkoxy group having at least 3 carbon atoms, and water, at a pH of about 8–12. Representative of such suitable glycol ethers are 2-butoxyethanol (ethylene glycol monobutyl ether); iso-butoxyethanol; propylene glycol butyl ether; (diethylene glycol) monobutyl ether; and 2-isopropoxy-ethanol. 2-Butoxyethanol (BGE) is the most preferred glycol ether. Ammonium hydroxide is the preferred neutralizing agent to adjust the pH of the reacton mixture to the desired range.

Suitable glycol ether:water weight ratios range from about 50–90 wt.% BGE:10–50 wt. % water. A 80:20 wt. ratio is preferred. The product of the polymerization is a composition of the polymer, e.g. poly(vinyl caprolactam) (PVCAP), in the polymerization solvent, e.g. BGE, water and the neutralizing agent. Generally, the solids content of the composition is about 30–90 wt. %, i.e. the weight of the polymer to the weight of the composition.

The composition of the invention may be provided with a suitable carrier solvent such as monoethylene glycol (MEG), methanol, ethanol, propanol, 1,4-butanediol, butanol, pentanol, hexanol, cyclohexyl pyrrolidone, propargyl alcohol, N-methylpyrrolidone and the like, preferably MEG. Preferably the concentration of MEG in the aqueous phase, i.e. under pipeline inhibition conditions, is about 2.5–10 wt. %, most preferably 4–5 wt. %.

The following examples are provided to illustrate the invention.

A. GENERAL METHOD

The gas hydrate inhibition tests were conducted in a 500 ml, 316 stainless steel autoclave vessel having a usable volume of 200 ml, equipped with a thermostated cooling jacket, sapphire window, inlet and outlet, platinum resistance thermometer (PRT) and magnetic stirring pellet. The rig is rated up to 400° C. and down to −25° C. Temperature and pressure are data logged, while the cell content is visually monitored by a boroscope video camera connected to a time lapsed video recorder. Hydrate formation in the rig is detected using a combination of three methods: visual detection of hydrate crystals, decrease in vessel pressure due to gas uptake and by the temperature exotherm created by heat released during hydrate formation.

The rig was cleaned prior to running a blank and/or test solutions. An air drill with wet and dry emery paper was used to remove traces of any adsorbed chemicals therein with a small amount of water being added to the rig. The vessel was then rinsed several times with double distilled water. A blank solution of 200 ml of double distilled water was run to confirm the reproducibility of the test. Formation of hydrates within 4–10 minutes was taken as a standard time for a given set of testing conditions, e.g. synthetic gas, 60 bar and T =4° C.

A synthetic gas mixture having the following composition was used for hydrate testing:

| Component | Mol % |
|---|---|
| $CO_2$ | 1.0 |
| Methane | 95.31 |
| Ethane | 2.96 |
| Propane | 0.53 |
| Iso-Butane | 0.1 |
| n-Butane | 0.1 |

B. EXPERIMENTAL PROCEDURE FOR EVALUATION OF HYDRATE INHIBITORS

Pipeline conditions were simulated by placing 200 ml of the use polymer solution (with total polymer concentration in the aqueous phase equal to about 0.5 wt. % [BGE]=0.75 wt. %) into a vessel fitted with a PTFE stirrer pellet. The rig top of the vessel was replaced and the securing ring tightened. A boroscope and video camera were then attached to the apparatus. The rig was then stirred and allowed to cool to a required temperature. Upon reaching the pre-set temperature, the stirrer was stopped and the video recorder and computer data logger started. The rig was then charged with Ravenspurn gas to reach the required pressure. A slightly higher pressure (2–3 bars) was used to allow for some gas dissolution in the water and the slight drop in pressure as the gas cooled. The stirrer was started at 500 rpm and the temperature (4° C.), pressure (85 bar) and start time ($t_o$) recorded. The run was terminated upon the formation of hydrates, usually at the moment of a pressure drop, which might or might not follow the exotherm, depending on the amount of hydrates formed and the amplitude of the effect. The final temperature, pressure and time (t) of hydrate formation was noted.

The onset of the hydrate formation time (t–$t_o$ mins) is indicated in the examples given below. The relative efficiencies of the inhibiting polymers are thus proportional to the measured induction times; a more effective polymer exhibits a relatively longer induction time.

Since the equilibrium melting temperature for hydrate of the synthetic gas in distilled water and P=85 bar is about 15.5° C., the sub-cooling is equal to 11.5° C. at P =85 bar and T=4° C. – measurements temperature.

C. EXPERIMENTAL RUNS PREPARATION OF INHIBITOR COMPOSITIONS

Examples 1 and 2 below illustrate the direct preparation and testing of low molecular weight poly(vinyl caprolactam) (PVCL) made in a mixed solvent of 2-butoxyethanol (BGE) and water, in the presence of a suitable neutralizing agent, e.g. ammonium hydroxide, added to adjust the initial pH of the reaction mixture to about 8–12, preferably about 10–12.

EXAMPLE 1

This example exemplifies the preparation of a 30 wt. %, low molecular weight poly(vinyl caprolactam) in a solvent mixture, by weight, of 2-butyoxy-ethanol/water (80/20) at a pH of 9.9.

1. Weight 240.0 g of 2-butoxyethanol and 60.0 g of deionized water in a 500-ml beaker. Adjusted its pH to 9.9 with 28% concentrated ammonium hydroxide. Transfer 240.0 g of the mixed solvent into a one-liter, Autoclave Engineers' stainless pressure reactor equipped with a variable speed, magnetic-driven agitator, thermocouple, nitrogen inlet tube, heating jacket and monomer feed port.
2. Fill pump with 300.00 g of vinyl caprolactam monomer, 60.0 g of 2-butoxyethanoll water (80/20) pre-mix, and 6.00 g of di-t-butyl peroxide.
3. Purge the reactor 3 times by applying nitrogen at 50-psi pressure and then releasing to 10-psi pressure. Keep the final reactor pressure at about 10 psi.
4. Start agitation at 100 rpm. Heat the mixed solvent to 140° C. in 45 minutes. Start recording reactor pressure and temperature.
5. Feed monomer pre-mix from Step #2 with a syringe pump into pressure reactor over a period of 2 hours at 140° C.
6. Add 1.00 g of di-t-butyl peroxide booster initiator at 60 and 150 minutes, respectively, from the end of monomer feeding while holding the reaction at 140° C. for 6 hours. The reactor pressure remained constant at about 80 psi throughout the holding period.
7. Cool the reactor content to ambient temperature. The viscous, darkamber liquid thus obtained was then discharged into a 1-liter glass bottle. Poly(vinyl caprolactam) thus obtained had a GPC—average molecular weight of 2,510 (polyethylene glycol standard) with a polydispersity index of 4.0.

Hydrate inhibition testing as described above of the product obtained in Example 1 at 4.0° C., 85 bar using the defined synthetic gas in distilled water with 0.30 wt. % PVCL, 0.75 wt. % BGE solvent gave t–$t_o$=800±340 min. induction time taken as an average of 6 runs under identical conditions.

EXAMPLE 2

This example exemplifies the preparation of 40 wt. %, low molecular weight poly(N-vinyl caprolactam) in a mixture of 2-butyoxyethanol/water (80/20=wt/wt) at a starting pH of 10.5.

1. Weight 192.0 g of 2-butoxyethanol and 48.0 g of deionized water in a 500-ml beaker. Adjusted its pH to 10.5 with 28% concentrated ammonium hydroxide. Transfer 200.0 g of the mixed solvent into a one-liter, Autoclave Engineers' stainless pressure reactor equipped with a variable speed, magnetic-driven agitator, thermocouple, nitrogen inlet tube, heating jacket and monomer feed port.
2. Fill pump with 360.00 g of vinyl caprolactam monomer, 40.0 g of 2-butoxyethanol/water (80/20) pre-mix, and 7.20 9 of di-t-butyl peroxide.
3. Purge the reactor 3 times by applying nitrogen at 50-psi pressure and then releasing to 10-psi pressure. Keep the final reactor pressure at about 10 psi.
4. Start agitation at 100 rpm. Heat the mixed solvent to 150° C. in 60 minutes. Start recording reactor pressure and temperature.
5. Feed monomer pre-mix from Step #2 with a syringe pump into pressure reactor over a period of 2 hours at 150° C.
6. Add 1.00 g of di-t-butyl peroxide booster initiator at 60 and 150 minutes, respectively, from the end of monomer feeding while holding the reaction at 1 50° C. for 6 hours. The reactor pressure remained constant at about 75 psi throughout the holding period.
7. Cool the reactor content to ambient temperature. The viscous, dark-amber liquid thus obtained was then discharged into a 1-liter glass bottle. Poly(vinyl caprolactam) thus obtained had a GPC weight—average molecular weight of 3,710 (polyethylene glycol standard) with a polydispersity index of 3.8.

Hydrate inhibition testing of the product obtained above at 4.0° C., 85 bar using the defined synthetic gas in distilled water with 0.40 wt% PVCL, 0.75 wt% BGE solvent gave $t-t_o=550\pm270$ min. induction time taken as an average of 3 runs under identical conditions.

COMPARATIVE EXAMPLE 300 g. of 2-butoxyethanol was charged into a 1-liter resin reaction tted with a propeller agitator, a reflux condenser, a nitrogen inlet tube and a thermowatch, and heated to 150° C. A monomer pre-mix was prepared by mixing 200 g. of vinyl caprolactam with 4.00 g of di-t-butyl peroxide initiator in a 400-mi beaker. Then the monomer pre-mix was pumped into the reaction kettle over a period of 2 hours. The reaction mixture then was held at 150° C. for 1.5 hours before adding 0.50 g of di-t-butyl peroxide initiator, and held at 150° C. for an additional 3 hours. After cooling to room temperature, the product was a light brown, viscous poly(vinyl caprolactam) in 2-butoxyethanol at 40% solids. Residual vinyl caprolactam was 0.9% by GC analysis. The PVCL polymer had a relative viscosity of 1.074 (1% in 2-butoxyethanol), a GPC molecular weight of 1,210 (polyethylene glycol standard), and a cloud point of 42° C.

Hydrate inhibition testing of the polymer product obtained at 4.0° C., 85 bar using synthetic gas in distilled water with 0.50 wt. % PVCL, 0.75 wt. % BGE gave $t-t_o=270\pm70$ min. induction time taken as an average of 6 runs under identical conditions.

While the invention has been described with particular reference to certain embodiments thereof, it will be understood that changes and modifications may be made which are within the skill of the art. Accordingly, it is intended to be bound only by the following claims, in which:

What is claimed is:

1. A composition for preventing or retarding the formation of gas hydrates or for reducing the tendency of gas hydrates to agglomerate, during the transport of a fluid comprising water and a hydrocarbon, through a conduit, where an aqueous phase is inherently present, comprising a solution of a homopolymer of vinyl caprolactam, or copolymer thereof, having a molecular weight in the range of about 500 to about 4000, (GPC., polyethylene glycol standard), which is made by polymerization of the monomer or monomers in a polymerization solvent which is a mixture of (a) a glycol ether containing an alkoxy group having at least 3 carbon atoms, (b) water, at a pH of about 8–12.

2. A composition according to claim 1 wherein the weight ratio of (a):(b) is about 50–90:50–10.

3. A composition according to claim 1 wherein the weight ratio of (a):(b) is about 80:20.

4. A composition according to claim 1 wherein the pH of the solution is adjusted with concentrated ammonium hydroxide.

5. A composition according to claim 1 wherein said glycol ether is 2-butoxyethanol.

6. A composition according to claim 1 wherein said polymer is made using di-t-butyl peroxide as initiator.

7. A composition according to claim 1 wherein said homopolymer or copolymer comprises about 30–90 wt. % of said solution.

8. A method of preventing or retarding the formation of gas hydrates or for reducing the tendency of gas hydrates to agglomerate, during the transport of a fluid comprising water and a hydrocarbon through a conduit which comprises including a composition of claim 1 therein.

9. A method according to claim 8 wherein said gas hydrate inhibiting polymer or copolymer concentration in the aqueous phase is about 0.1 to 3% by weight.

10. A method according to claim 9 wherein the solvent inhibition concentration is about 1 to 9% by weight in the aqueous phase.

* * * * *